United States Patent
Iida et al.

(10) Patent No.: US 8,080,676 B2
(45) Date of Patent: Dec. 20, 2011

(54) METHOD OF PRODUCING S-(−)-6-HYDROXY-2,5,7,8-TETRAMETHYL CHROMANE-2-CARBOXYLIC ACID AND PRODUCT OBTAINED BY THE METHOD

(75) Inventors: Akifumi Iida, Niigata (JP); Youichi Kyuuko, Niigata (JP); Toshio Hidaka, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 298 days.

(21) Appl. No.: 12/312,125

(22) PCT Filed: Oct. 25, 2007

(86) PCT No.: PCT/JP2007/070801
§ 371 (c)(1),
(2), (4) Date: Apr. 27, 2009

(87) PCT Pub. No.: WO2008/050829
PCT Pub. Date: May 2, 2008

(65) Prior Publication Data
US 2010/0063305 A1    Mar. 11, 2010

(30) Foreign Application Priority Data
Oct. 26, 2006  (JP) .................. 2006-291628

(51) Int. Cl.
*C07D 311/66*  (2006.01)
(52) U.S. Cl. ......................................... 549/405
(58) Field of Classification Search ............ 549/405
See application file for complete search history.

(56) References Cited

U.S. PATENT DOCUMENTS

| | | | |
|---|---|---|---|
| 4,026,907 A | 5/1977 | Scott et al. | |
| 5,348,973 A | 9/1994 | Raju et al. | |
| 7,615,650 B2 | 11/2009 | Tanaka et al. | |
| 2006/0141591 A1 | 6/2006 | Kyuuko | |
| 2007/0179304 A1 | 8/2007 | Tanaka et al. | |

FOREIGN PATENT DOCUMENTS

| | | |
|---|---|---|
| EP | 1634958 A1 | 3/2006 |
| EP | 1710239 A1 | 10/2006 |
| JP | S60-92283 A | 5/1985 |
| JP | H07-97380 A | 4/1995 |
| JP | 11-80149 A | 3/1999 |
| JP | 2003-146981 A | 5/2003 |
| JP | 2006-306808 A | 11/2006 |
| JP | 2006-306809 A | 11/2006 |
| WO | WO 02/12221 | 2/2002 |
| WO | WO 2004-108944 A1 * | 12/2004 |

OTHER PUBLICATIONS

European Communication dated Jan. 4, 2010.

\* cited by examiner

*Primary Examiner* — Bernard Dentz
(74) *Attorney, Agent, or Firm* — Fitch, Even, Tabin & Flannery

(57) ABSTRACT

The present invention provides an industrially available method for efficiently producing high-purity S-(−)-6-hydroxy-2,5,7,8-tetramethylchromane-2-carboxylic acid excellent in solid-liquid separability from an S-(−)-6-hydroxy-2,5,7,8-tetramethylchromane-2-carboxylic acid ester, and also provides products obtained by the method.

Under a temperature condition of 50-80° C. in an aqueous solvent, (A) an S-(−)-6-hydroxy-2,5,7,8-tetramethylchromane-2-carboxylic acid ester represented by the general formula (1) is hydrolyzed under a basic condition for 1-3 hours; then (B) the insoluble matters contained in the reaction solution resulting from the hydrolysis are removed; and (C) an acid is added to the resulting solution to effect crystallization; provided that R in the general formula (1) represents an alkyl or aryl group.

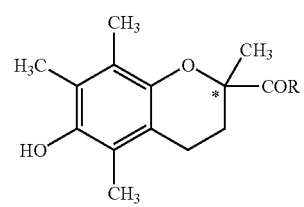

(1)

9 Claims, 1 Drawing Sheet

METHOD OF PRODUCING S-(−)-6-HYDROXY-2,5,7,8-TETRAMETHYL CHROMANE-2-CARBOXYLIC ACID AND PRODUCT OBTAINED BY THE METHOD

CROSS-REFERENCE TO RELATED APPLICATIONS

This is a U.S. National Phase of International Application PCT/JP2007/070801, filed Oct. 25, 2007, and claims foreign priority under 35 U.S.C. §119 based on Japanese Application No. 2006-291628, filed Oct. 26, 2006, the entire disclosures of which applications are hereby incorporated herein by reference.

TECHNICAL FIELD

The present invention relates to a production method for efficiently obtaining a high purity S-(−)-6-hydroxy-2,5,7,8-tetramethylchromane-2-carboxylic acid excellent in solid-liquid separability with high yield by way of hydrolysis reaction of an S-(−)-6-hydroxy-2,5,7,8-tetramethylchromane-2-carboxylic acid ester, and a product obtained by the method. An optically active substance, S-(−)-6-hydroxy-2,5,7,8-tetramethylchromane-2-carboxylic acid, especially, a high purity S-(−)-6-hydroxy-2,5,7,8-tetramethylchromane-2-carboxylic acid is very important as a raw material for vitamins or drugs such as anti-inflammatory agents and anti-allergic agents.

BACKGROUND ART

Conventional examples of methods for producing chromane compounds include a multi-step method in which a phenol and an unsaturated carbonyl compound are used as starting materials (see, for example, Patent Document 1); and a method in which a phenol, a formaldehyde, and an unsaturated compound are allowed to react without use of any catalyst or in the presence of an acid or amine (see, for example, Patent Documents 2, 3 and 4).

An optically active 6-hydroxy-2,5,7,8-tetramethylchromane-2-carboxylic acid derivatives can be obtained by way of an optical resolution of 6-hydroxy-2,5,7,8-tetramethylchromane-2-carboxylic acid ester obtained by the method of Patent Document 4, in accordance with 1) a diastereomeric resolution with an optically active amine (see, for example, Patent Documents 5 and 6); or 2) an enantiospecific hydrolysis of (±)-6-hydroxy-2,5,7,8-tetramethylchromane-2-carboxylic acid ester using an enzymatic catalyst (see, for example, Patent Document 7).

Although it is possible to produce S-(−)-6-hydroxy-2,5,7,8-tetramethylchromane-2-carboxylic acid in accordance with the above mentioned methods, there are still some points which require improvement when high purity S-(−)-6-hydroxy-2,5,7,8-tetramethylchromane-2-carboxylic acid is provided industrially and economically. The present inventors have already proposed methods for producing 6-hydroxy-2,5,7,8-tetramethylchromane-2-carboxylic acid easily in good yield. However, even in these methods, when S-(−)-6-hydroxy-2,5,7,8-tetramethylchromane-2-carboxylic acid ester is produced and then hydrolyzed to produce S-(−)-6-hydroxy-2,5,7,8-tetramethylchromane-2-carboxylic acid, the resulting S-(−)-6-hydroxy-2,5,7,8-tetramethylchromane-2-carboxylic acid is deteriorated in yield and purity, producing a reacted solution in the form of a pasty inseparable slurry, if operation conditions after the hydrolysis are improper.

Therefore, for the practice on an industrial scale, it is required to establish means for solving these problems to obtain the target product economically. However, none of the conventional and prior art references has disclosed a production condition for S-(−)-6-hydroxy-2,5,7,8-tetramethylchromane-2-carboxylic acid excellent in efficiency such that solid/liquid separation and drying of crystals are made easier.

Patent Document 1: U.S. Pat. No. 4,026,907 specification
Patent Document 2: Japanese Patent Laid-Open (Kokai) No. S60-92283
Patent Document 3: Japanese Patent Laid-Open (Kokai) No. H7-97380
Patent Document 4: Japanese Patent Laid-Open (Kokai) No. 2003-146981
Patent Document 5: Japanese Patent Laid-Open (Kokai) No. H11-80149
Patent Document 6: International Publication No. WO02/12221 pamphlet
Patent Document 7: U.S. Pat. No. 5,348,973 specification

DISCLOSURE OF THE INVENTION

Problem to be Solved by the Invention

The object of the present invention is to provide a production method which can be carried out on an industrial scale for efficiently producing high-purity S-(−)-6-hydroxy-2,5,7,8-tetramethylchromane-2-carboxylic acid excellent in solid/liquid separability from an S-(−)-6-hydroxy-2,5,7,8-tetramethylchromane-2-carboxylic acid ester, and products obtained by the method.

Means for Solving the Problem

As a result of diligent researches for the above mentioned object, the present inventors have found that optically and chemically very high-purity crystals excellent in filterability of crystal slurry, good in drying as well as almost free from scattering of crystals and excellent in handleability can be obtained by adopting the following operation conditions at the time when S-(−)-6-hydroxy-2,5,7,8-tetramethylchromane-2-carboxylic acid is produced by hydrolysis of an S-(−)-6-hydroxy-2,5,7,8-tetramethylchromane-2-carboxylic acid ester, and have finally completed the present invention.

That is, the present invention relates to a method for producing high-purity crystals of S-(−)-6-hydroxy-2,5,7,8-tetramethylchromane-2-carboxylic acid excellent in solid-liquid separability from a reaction solution resulting from hydrolysis of an S-(−)-6-hydroxy-2,5,7,8-tetramethylchromane-2-carboxylic acid ester under a basic condition as well as products obtained by the method, as shown in the following (1)-(6).

(1) A method for producing S-(−)-6-hydroxy-2,5,7,8-tetramethylchromane-2-carboxylic acid under a temperature condition of 50-80° C. in an aqueous solvent by hydrolysis of an S-(−)-6-hydroxy-2,5,7,8-tetramethylchromane-2-carboxylic acid ester, which comprises: (A) hydrolyzing an S-(−)-6-hydroxy-2,5,7,8-tetramethylchromane-2-carboxylic acid ester represented by general formula (1) under a basic condition for 1-3 hours, then (B) removing insoluble matters contained in the reaction solution resulting from the hydrolysis, and (C) adding an acid to the resulting solution to effect crystallization,

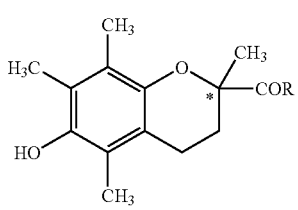

(1)

wherein R in general formula (1) represents an alkyl group or aryl group.

(2) A method for producing S-(−)-6-hydroxy-2,5,7,8-tetramethylchromane-2-carboxylic acid, according to item (1), in which the aqueous solvent comprises an alcohol.
(3) A method for producing S-(−)-6-hydroxy-2,5,7,8-tetramethylchromane-2-carboxylic acid, according to item (2), in which the alcohol is methanol.
(4) A method for producing S-(−)-6-hydroxy-2,5,7,8-tetramethylchromane-2-carboxylic acid, according to item (1), in which the removal of insoluble matters contained in the reaction solution resulting from the hydrolysis in (B) is conducted after adjusting a pH of the reaction solution to 5-7.
(5) A method for producing S-(−)-6-hydroxy-2,5,7,8-tetramethylchromane-2-carboxylic acid, according to item (1), in which crystals of S-(−)-6-hydroxy-2,5,7,8-tetramethylchromane-2-carboxylic acid are added as seed crystals when an acid is added to the resulting solution to effect crystallization in (C).
(6) S-(−)-6-hydroxy-2,5,7,8-tetramethylchromane-2-carboxylic acid, which is obtained by the production method according to any one of the items (1)-(5).

Effect of the Invention

The method of the present invention which efficiently provides crystals excellent in solid-liquid separability and purity in a simple way makes it possible to economically produce and supply an S-(−)-6-hydroxy-2,5,7,8-tetramethylchromane-2-carboxylic acid that is higher in optical and chemical purity and useful as a material for pharmaceuticals, agricultural chemicals and the like, without any further purification process such as recrystallization.

BEST MODES FOR CARRYING OUT THE INVENTION

Figure 1:
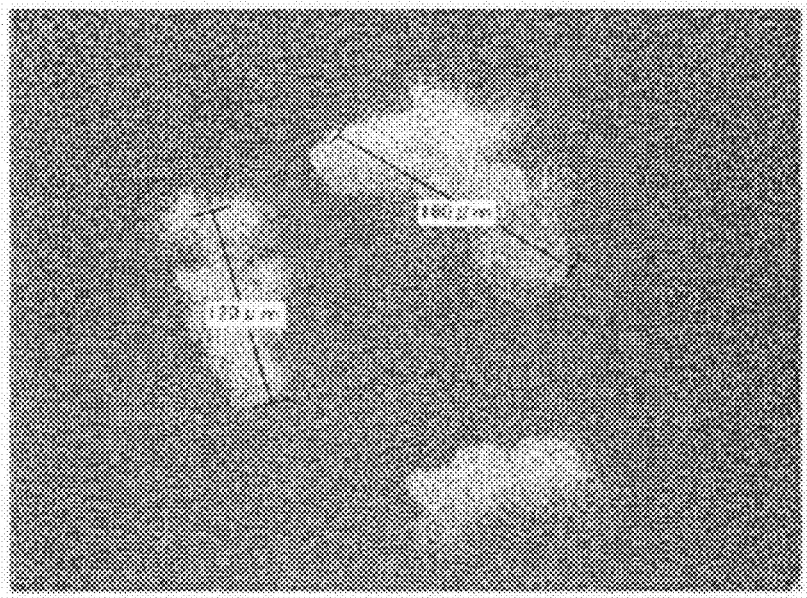
FIG. 1 is a microscopic photograph of crystals excellent in solid-liquid separability, obtained in Example 7.

The raw material which is used in the present invention is an S-(−)-6-hydroxy-2,5,7,8-tetramethylchromane-2-carboxylic acid ester. Such an optically active ester can be obtained by using an enzymatic catalyst that enantioselectively esterifies a racemic body or another mixture of optically active 6-hydroxy-2,5,7,8-tetramethylchromane-2-carboxylic acid as a raw material.

The alkyl or aryl group of S-(−)-6-hydroxy-2,5,7,8-tetramethylchromane-2-carboxylic acid ester (that is, R of the above general formula (1)) is preferably an aliphatic or aromatic hydrocarbons with 1-24 carbon atoms which may have a functional group such as a halogen atom and a hydroxide group as a substituent. Examples of the hydrocarbon residue of the ester preferably include methyl, ethyl, n-propyl, i-propyl, n-butyl, i-butyl, t-butyl, n-amyl, allyl, n-hexyl, n-octyl, 2-ethylhexyl, lauryl, stearyl, cyclohexyl, phenyl and benzyl groups, and particularly preferably methyl group and ethyl group.

Next, a case in which methyl 6-hydroxy-2,5,7,8-tetramethylchromane-2-carboxylate is used as a raw material will be described by way of example. Methyl 6-hydroxy-2,5,7,8-tetramethylchromane-2-carboxylate serving as a raw material can be obtained by performing an esterification of 6-hydroxy-2,5,7,8-tetramethylchromane-2-carboxylic acid and methanol in the presence of an enzymatic catalyst (lipase) in an organic solvent. Charge ratio of the enzyme relative to the raw material can be decided arbitrarily, but it is preferable to adjust the amount of enzyme so as to meet an aimed yield in about 24 hours from the viewpoint of reaction efficiency. Meanwhile, methyl-S-(−)-6-hydroxy-2,5,7,8-tetramethylchromane-2-carboxylate can be produced in accordance with the procedures which are indicated in Example 1 and based on the method already proposed by the present inventors.

The hydrolysis reaction of methyl-S-(−)-6-hydroxy-2,5,7,8-tetramethylchromane-2-carboxylate can be conducted under an acidic condition, but is preferably conducted in an aqueous solvent under a basic condition from the viewpoint that the hydrolysis can be effected efficiently under a relatively mild condition. The base used in hydrolysis can be an inorganic compound or organic compound of weak base to strong base, but is preferably a hydroxide of a strongly basic alkali metal or alkali earth metal from the viewpoint that reactivity is good and non-reacted substances hardly remain. Particularly preferable are KOH and NaOH. The amount of base to be used for hydrolysis is preferably a 1-5 times molar excess to the substrate and particularly preferably a 1-2 times molar excess.

The reaction temperature during hydrolysis is preferably 50-80° C., and the reaction time is preferably in a range of 1-3 hours including from addition of the base to elevation of temperature. If the hydrolysis condition under the basic condition is set weaker or stronger than these ranges, the finally obtained product, S-(−)-6-hydroxy-2,5,7,8-tetramethylchromane-2-carboxylic acid will be deteriorated in purity or yield.

The amount of the aqueous solvent to be used in hydrolysis is preferably 2 to 10-fold amount by weight, and more preferably 3 to 5-fold amount by weight relative to the substrate. In addition, the reaction may proceed more smoothly by adding an organic solvent that mixes well with water, dissolves the substrate and is inert for the reaction. Examples of such an organic solvent include alcohols and nitriles, but methyl alcohol is particularly preferable from the viewpoint that it is good in miscibility with the substrate but there is no risk of trans-esterification and no complication of solvent composition. For example, methanol is used in an amount of preferably 0.1 to 1-fold amount by weight and more preferable 0.1 to 0.5-fold amount by weight relative to water. When the amount of methanol to be used is less than 0.1-fold amount by weight, dissolving rate of methyl-S-(−)-6-hydroxy-2,5,7,8-tetramethylchromane-2-carboxylate as the substrate in the aqueous solvent may be reduced. Conversely, when it is more than 1-fold amount by weight, methanol is so excessive as to reduce the boiling point, and thus this is not economical nor preferable in terms of costs for facilities and operation.

After the completion of hydrolysis, insoluble matters contained in the reaction solution are removed by a separation method such as filtration. Insoluble matters are composed of substances low in solubility contained in the raw material, by-products generated during the reaction, unreacted substances of the raw material and the like. After the completion of the reaction, it is important to remove insoluble matters contained in the solution as much as possible. The removal operation of insoluble matters must be conducted without fail since it directly influences the purity of the finally yielded product. Meanwhile, the separation method of insoluble matters includes operations such as ordinary decantation, filtration under normal pressure, filtration under reduced pressure, filtration under increased pressure and centrifugation, but is not particularly limited to these operations as long as insoluble matters can be separated.

The liquid temperature at the time of removing insoluble matters is preferably in a temperature range of 50-80° C. comparable to the reaction temperature of the above hydrolysis. In this instance, it is advantageous to remove insoluble matters at a temperature close to the reaction temperature of hydrolysis from the viewpoint of removal efficiency and heat efficiency.

Removal of insoluble matters may be conducted by treating the reaction solution directly after hydrolysis, but is preferably conducted after adding an acid to the reaction solution so as to adjust the pH to 5-7. This operation allows the dissolved impurity components to precipitate as insoluble matters, and thus makes it possible to obtain a higher-purity S-(−)-6-hydroxy-2,5,7,8-tetramethylchromane-2-carboxylic acid. In this instance, if an acid is excessively added so as to lower the pH to less than 5, not only insoluble matters but also S-(−)-6-hydroxy-2,5,7,8-tetramethylchromane-2-carboxylic acid are started to precipitate, thereby leading to decrease of yield, and thus this is not preferable. The acid used for the pH adjustment is preferably the same as in the next step in which an acid is added to effect crystallization (hereinafter referred to as "precipitation by acid") from the viewpoint of operation.

The reaction solution is subjected to precipitation by acid after insoluble matters are thus-removed. In this instance, it is favorable that the precipitation by acid is conducted after adding a small amount of crystals of S-(−)-6-hydroxy-2,5,7,8-tetramethylchromane-2-carboxylic acid as seed crystals. This makes it possible to obtain crystals of S-(−)-6-hydroxy-2,5,7,8-tetramethylchromane-2-carboxylic acid, which are easy to precipitate and excellent in solid-liquid separability, compared with the case where no seed crystals are added.

For the above mentioned pH adjustment and the precipitation by acid, may be used any of strongly acidic mineral acids such as hydrochloric acid, sulfuric acid and nitric acid, or weak acids such as sodium hydrogen sulfate and potassium hydrogen sulfate. When acids such as sodium hydrogen sulfate and potassium hydrogen sulfate are used, it is preferable to use these acids dissolved in 1-10 times volume of water.

The total amount of acid to be used for the pH adjustment and the precipitation by acid is necessarily more than the base used in the step of hydrolysis. An addition of a very excessive amount will have no adverse effect on the reaction, but about 1.1 times molar excess to the base will be sufficient in consideration of economy.

It is preferable to perform the precipitation by acid at a temperature range of 50-80° C. When it is performed at a temperature below 50° C., precipitated crystals may become minute crystals difficult to deposit, and thus the whole liquid becomes pasty. These pasty crystals are very bad in filterability and drying, and when they are subjected to solid-liquid separation, they become crystals that are accompanied with a large amount of mother liquor and high in liquid content. Therefore, inorganic salts and impurities contained in the mother liquor are apt to remain, thereby lowering the purity of the resultant crystals.

On the other hand, when it exceeds 80° C., crystals which should have precipitated by the precipitation by acid become oily and form a state of two layers. If the precipitation by acid is continued in this state, the oil part of the bottom layer sometimes crystallizes at once and becomes massive. Being massive is not preferable because the crystal becomes difficult to be taken out of the reaction vessel, and besides becomes lower in chemical purity.

The pressure during the precipitation by acid is usually atmospheric pressure, but the precipitation by acid may be performed under increased pressure or reduced pressure, as required. The above respective operations are preferably performed under inert gas atmosphere, if possible. After the precipitation by acid, the neutralized salts which are contained in the crystal slurry resulting from the solid-liquid separation are washed out and removed thoroughly with water, and then crystals are dried to provide the final product.

The way of adding a solution at the time of the precipitation by acid may be any of the ways of adding an acidic solution for the precipitation by acid to a solution that has been treated for removal of insoluble matters, adding the treated solution to an acidic solution for the precipitation by acid, or adding both the treated solution and the acidic solution to water or a mixed solution obtained by adding an organic solvent to water.

The way of adding can be adding at once, but is preferably dropping gradually over a time period of about an hour since crystals better in solid-liquid separability are obtained. Examples of the organic solvent include those mixing well with water, such as alcohols and nitriles, but methanol is preferable which is the same as the solvent added during the hydrolysis.

By use of the method of the present invention, it is made possible to obtain crystals which have a large particle diameter and are excellent in solid-liquid separability. In addition, crystals are improved in filterability, and thus it becomes easier to wash out the contaminating mother liquor which accompanies salts and the like, and the time required for filtration is greatly shortened. Therefore, it has become possible to efficiently produce a high-purity S-(−)-6-hydroxy-2,5,7,8-tetramethylchromane-2-carboxylic acid low in powder scattering and excellent in handleability, which the conventional techniques were unable to produce.

EXAMPLE

The present invention will be described in more detail by way of Examples and Comparative Examples. However, the present invention is not restricted to these Examples. The optical purity was determined by HPLC using SUMICHIRAL OA-3200 (4.6 φmm×250 mm) available from Sumika Chemical Analysis Service Ltd.

Example 1

1) Production of methyl (±)-6-hydroxy-2,5,7,8-tetramethylchromane-2-carboxylate

In a 1 L stainless-steel autoclave, 100 g (0.657 mol) of 1,4-dihydroxy-2,3,5-trimethylbenzene, 110 g of an aqueous formalin solution (formaldehyde 37 wt %, water 56 wt %, and methanol 7 wt %), and 330 g (3.296 mol) of methyl methacrylate were placed. The mixture was allowed to react at 180° C. for 3 hours under stirring. After the mixture was cooled to 40° C., precipitated crystals were filtered, and rinsed twice with 200 g of methanol. The collected crystals were dried to obtain the aimed methyl 6-hydroxy-2,5,7,8-tetramethylchromane-2-carboxylate (hereinafter, referred to as CCM) in an amount of 135 g (0.478 mol as CCM, yield: 72.6%, chemical purity: 93.5%).

2) Production of (±)-6-hydroxy-2,5,7,8-tetramethyl-chromane-2-carboxylic acid

In a 200 mL glass vessel equipped with a condenser, 16.7 g (59.1 mmol as CCM, chemical purity: 93.5%) of CCM produced as above, 16.7 g of methanol, 3.3 g (82.5 mmol) of NaOH and 50 g of water were placed, and the mixture was subjected to hydrolysis of esters under nitrogen atmosphere at 80° C. for an hour under stirring. The reaction solution was filtrated at the same temperature as it was to remove insoluble matters, and then added dropwise over an hour to an acidic solution which was obtained by dissolving 11.7 g (85.9 mmol) of potassium hydrogen sulfate in 50 g of water and was kept at 80° C. in a 300 mL glass vessel equipped with a condenser. After completion of the neutralization treatment, crystals were precipitated immediately when stirring was stopped to leave the reaction mixture to stand. The crystals were filtered at 80° C., washed twice with 50 mL of water, and then vacuum-dried at 80° C. for 24 hours to obtain 6-hydroxy-2,5,7,8-tetramethylchromane-2-carboxylic acid (hereinafter referred to as CCA) in an amount of 14.5 g (57.9 mmol) (yield: 98.3%, chemical purity: 99.7%).

3) Production of methyl S-(−)-6-hydroxy-2,5,7,8-tetramethylchromane-2-carboxylate In a 30 L stainless-steel pressure vessel, 1200 g (4.79 mol) of CCA obtained as above, 767 g (23.93 mol) of methanol, 15000 g of isopropyl ether and 400 g of immobilized enzyme CHIRAZYMEL-2, c-f, C2 (manufactured by Roche Diagnostics) were placed and purged with argon gas, and then the mixture was allowed to react at 80° C. for 24 hours. After 24 hours, the immobilized enzymatic catalyst was removed by filtration to collect the reaction solution. To this reaction solution, an aqueous solution of 760 g (7.17 mol) of sodium carbonate in 6000 g of water was added to allow the non-reacted CCA to move into the aqueous layer. After separation of the organic layer from the aqueous layer, the organic layer was concentrated, and precipitated crystals were collected by filtration to obtain methyl S-(−)-6-hydroxy-2,5,7,8-tetramethylchromane-2-carboxylate (hereinafter referred to as S-CCM) in an amount of 500 g (1.89 mol) (yield: 39.5 mol %, chemical purity: 99.0%, optical purity: 99% ee).

4) Production of S-(−)-6-hydroxy-2,5,7,8-tetramethylchromane-2-carboxylic acid

In a 3 L glass vessel equipped with a condenser, 418 g (1.58 mol) of S-CCM produced as above, 417.5 g of methanol, 82.0 g (2.05 mol) of NaOH and 1250 g of water were placed, and the mixture was allowed to react under nitrogen atmosphere at 80° C. for an hour under stirring. Next, under a temperature condition of 80° C., an acidic solution of 292.5 g (2.15 mol) of potassium hydrogen sulfate in 1250 g of water was added thereto until the pH reached 5. Then, insoluble matters were removed by filtration, the filtrate was cooled to 60° C., and the remaining acidic solution was added dropwise over an hour to cause precipitation by acid. After the completion of dropping, stirring was stopped to precipitate crystals excellent in sedimentation separability. The crystals were filtered, and washed twice with 1250 mL of water. The resulting crystal slurry had a liquid content of 31 wt %, and was very good in both filterability and drying of crystals. After drying, 365 g (1.46 mol, yield: 92.4 mol %, chemical purity 99.7%, optical purity 99% ee) of granular crystals of S-CCA were obtained.

Example 2

In a 3 L glass vessel equipped with a condenser, 418 g (1.58 mol) of S-CCM obtained as in Example 1, 417.5 g of methanol, 82.0 g (2.05 mol) of NaOH and 1250 g of water were placed, and the mixture was allowed to react under nitrogen atmosphere at 80° C. for an hour under stirring. Next, under a temperature condition of 80° C., an acidic solution of 292.5 g (2.15 mol) of potassium hydrogen sulfate in 1250 g of water was added thereto until the pH reached 5, and then insoluble matters were removed by filtration. Further, the filtrate was kept at 50° C., and the remaining acidic solution was added dropwise over an hour. After completion of the dropping, the stirring was stopped to precipitate crystals excellent in sedimentation separability. The crystals were filtered, and washed twice with 1250 mL of water. The resulting crystal slurry had a liquid content of 30 wt %, and was very good in both filterability and drying of crystals. After drying, 368 g (1.47 mol, yield: 93.0 mol %, chemical purity 99.5%, optical purity 99% ee) of granular crystals of S-CCA were obtained.

Example 3

In a 3 L glass vessel equipped with a condenser, 418 g (1.58 mol) of S-CCM obtained as in Example 1, 417.5 g of methanol, 82.0 g (2.05 mol) of NaOH and 1250 g of water were placed, and the mixture was allowed to react under nitrogen atmosphere at 80° C. for an hour under stirring. Next, under a temperature condition of 80° C., an acidic solution of 292.5 g (2.15 mol) of potassium hydrogen sulfate in 1250 g of water was added thereto until the pH reached 5, and then insoluble matters were removed by filtration. Further, the filtrate was kept at 70° C., and the remaining acidic solution was added dropwise over an hour to cause precipitation by acid. After completion of the dropping, the stirring was stopped to precipitate crystals excellent in sedimentation separability. The crystals were filtered, and washed twice with 1250 mL of water. The resulting crystal slurry had a liquid content of 29 wt %, and was very good in both filterability and drying of crystals. After drying, 363 g (1.45 mol, yield: 91.8 mol %, chemical purity 99.6%, optical purity 99% ee) of granular crystals of S-CCA were obtained.

Example 4

In a 3 L glass vessel equipped with a condenser, 418 g (1.58 mol) of S-CCM obtained as in Example 1, 417.5 g of methanol, 82.0 g (2.05 mol) of NaOH and 1250 g of water were placed, and the mixture was allowed to react under nitrogen atmosphere at 80° C. for an hour under stirring. Next, under a temperature condition of 80° C., an acidic solution of 292.5 g (2.15 mol) of potassium hydrogen sulfate in 1250 g of water was added thereto until the pH reached 5, and then insoluble matters were removed by filtration. Further, the filtrate was kept at 80° C., and the remaining acidic solution was added dropwise over an hour to cause precipitation by acid. After completion of the dropping, the stirring was stopped to precipitate crystals excellent in sedimentation separability. The crystals were filtered, and washed twice with 1250 mL of water. The resulting crystal slurry had a liquid content of 32 wt %, and was very good in both filterability and drying of crystals. After drying, 366 g (1.46 mol, yield: 92.6 mol %, chemical purity 99.2%, optical purity 99% ee) of granular crystals of S-CCA were obtained.

Example 5

In a 3 L glass vessel equipped with a condenser, 418 g (1.58 mol) of S-CCM obtained as in Example 1, 417.5 g of methanol, 82.0 g (2.05 mol) of NaOH and 1250 g of water were placed, and the mixture was allowed to react under nitrogen atmosphere at 80° C. for an hour under stirring. Next, under a temperature condition of 80° C., an acidic solution of 292.5 g (2.15 mol) of potassium hydrogen sulfate in 1250 g of water was added thereto until the pH reached 5, and then insoluble matters were removed by filtration. Further, 1 g of seed crystals were added to the filtrate, and then the remaining acidic solution was added dropwise over an hour to cause precipitation by acid while keeping the filtrate at 60° C. After completion of the dropping, the stirring was stopped to precipitate crystals excellent in sedimentation separability. The crystals were filtered, and washed twice with 1250 mL of water. The resulting crystal slurry had a liquid content of 31 wt %, and was very good in both filterability and drying of crystals. After drying, 368 g (1.47 mol, yield: 93.0 mol %, chemical purity 99.7%, optical purity 99% ee) of granular crystals of S-CCA were obtained.

Example 6

In a 3 L glass vessel equipped with a condenser, 418 g (1.58 mol) of S-CCM obtained as in Example 1, 417.5 g of methanol, 82.0 g (2.05 mol) of NaOH and 1250 g of water were placed, and the mixture was allowed to react under nitrogen atmosphere at 80° C. for an hour under stirring. Next, under a temperature condition of 80° C., an acidic solution of 292.5 g (2.15 mol) of potassium hydrogen sulfate in 1250 g of water was added thereto until the pH reached 7, and then insoluble matters were removed by filtration. Further, the filtrate was kept at 60° C., and the remaining acidic solution was added dropwise over an hour to cause precipitation by acid. After completion of the dropping, the stirring was stopped to precipitate crystals excellent in sedimentation separability. The crystals were filtered, and washed twice with 1250 mL of water. The resulting crystal slurry had a liquid content of 32 wt %, and was very good in both filterability and drying of crystals. After drying, 368 g (1.47 mol, yield: 93.0 mol %, chemical purity 99.5%, optical purity 99% ee) of granular crystals of S-CCA (refers to FIG. 1) were obtained.

Example 7

In a 3 L glass vessel equipped with a condenser, 418 g (1.58 mol) of S-CCM obtained as in Example 1, 417.5 g of methanol, 82.0 g (2.05 mol) of NaOH and 1250 g of water were placed, and the mixture was allowed to react under nitrogen atmosphere at 80° C. for an hour under stirring. Next, under a temperature condition of 60° C., an acidic solution of 292.5 g (2.15 mol) of potassium hydrogen sulfate in 1250 g of water was added thereto until the pH reached 5, and then insoluble matters were removed by filtration. Further, the filtrate was kept at 60° C., and the remaining acidic solution was added dropwise over an hour to cause precipitation by acid. The crystals were filtered, and washed twice with 1250 mL of water. The resulting crystal slurry had a liquid content of 31 wt %, and was very good in both filterability and drying of crystals. After drying, 375 g (1.50 mol, yield: 94.9 mol %, chemical purity 99.6%, optical purity 99% ee) of granular crystals of S-CCA (refers to FIG. 1) were obtained.

Example 8

In a 3 L glass vessel equipped with a condenser, 418 g (1.58 mol) of S-CCM obtained as in Example 1, 417.5 g of methanol, 82.0 g (2.05 mol) of NaOH and 1250 g of water were placed, and the mixture was allowed to react under nitrogen atmosphere at 80° C. for an hour under stirring. Next, under a temperature condition of 80° C., an acidic solution of 292.5 g (2.15 mol) of potassium hydrogen sulfate in 1250 g of water was added thereto until the pH reached 5, and then insoluble matters were removed by filtration. 1 g of seed crystals were added to the filtrate, and then the remaining acidic solution was added dropwise over an hour to cause precipitation by acid while keeping the filtrate at 80° C. After completion of the dropping, the stirring was stopped to precipitate crystals excellent in sedimentation separability. The crystals were filtered, and washed twice with 1250 mL of water. The resulting crystal slurry had a liquid content of 31 wt %, and was very good in both filterability and drying of crystals. After drying, 369 g (1.47 mol, yield: 93.3 mol %, chemical purity 99.2%, optical purity 99% ee) of granular crystals of S-CCA were obtained.

Example 9

In a 3 L glass vessel equipped with a condenser, 418 g (1.58 mol) of S-CCM obtained as in Example 1, 417.5 g of methanol, 101.1 g (2.53 mol) of NaOH and 1250 g of water were placed, and the mixture was allowed to react under nitrogen atmosphere at 60° C. for 2 hours under stirring. Next, under a temperature condition of 60° C., an acidic solution of 361.3 g (2.65 mol) of potassium hydrogen sulfate in 1250 g of water was added thereto until the pH reached 5, and then insoluble matters were removed by filtration. 1 g of seed crystals were added to the filtrate, and then the remaining acidic solution was added dropwise over an hour to cause precipitation by acid while keeping the filtrate at 60° C. After completion of the dropping, the stirring was stopped to precipitate crystals excellent in sedimentation separability. The crystals were filtered, and washed twice with 1250 mL of water. The resulting crystal slurry had a liquid content of 31 wt %, and was very good in filterability and drying of crystals. After drying, 366 g (1.45 mol, yield: 92.6 mol %, chemical purity 99.0%, optical purity 99% ee) of granular crystals of S-CCA were obtained.

Example 10

In a 3 L glass vessel equipped with a condenser, 418 g (1.58 mol) of S-CCM obtained as Example 1, 417.5 g of methanol, 113.7 g (2.84 mol) of NaOH and 1250 g of water were placed, and the mixture was allowed to react under nitrogen atmosphere at 50° C. for 3 hours under stirring. Next, under a temperature condition of 50° C., an acidic solution of 406.5 g (2.99 mol) of potassium hydrogen sulfate in 1250 g of water was added thereto until the pH reached 5, and then insoluble matters were removed by filtration. 1 g of seed crystals were added to the filtrate, and then the remaining acidic solution was added dropwise over an hour to cause precipitation by acid while keeping the filtrate at 50° C. After completion of the dropping, the stirring was stopped to precipitate crystals excellent in sedimentation separability. The crystals were filtered, and washed twice with 1250 mL of water. The resulting crystal slurry had a liquid content of 31 wt %, and was very good in filterability and drying of crystals. After drying, 364 g (1.44 mol, yield: 92.1 mol %, chemical purity 98.9%, optical purity 99% ee) of granular crystals of S-CCA were obtained.

Comparative Example 1

Figure 2:
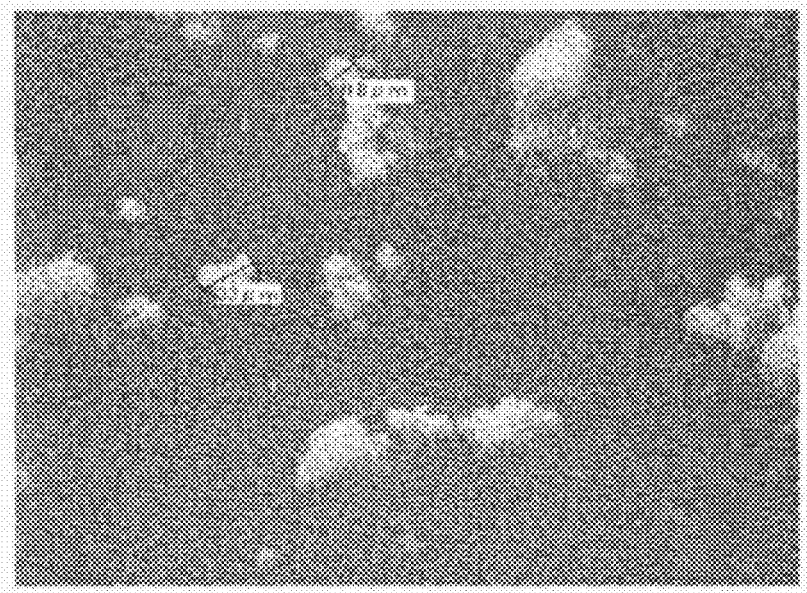
FIG. 2 is a microscopic photograph of crystals bad in solid-liquid separability, obtained in Comparative Example 1.

In a 3 L glass vessel equipped with a condenser, 418 g (1.58 mol) of S-CCM obtained as in Example 1, 417.5 g of methanol, 82.0 g (2.05 mol) of NaOH and 1250 g of water were placed, and the mixture was allowed to react under nitrogen atmosphere at 80° C. for an hour under stirring. Next, under a temperature condition of 80° C., an acidic solution of 292.5 g (2.15 mol) of potassium hydrogen sulfate in 1250 g of water was added thereto until the pH reached 5. After insoluble matters were removed by filtration, the filtrate was kept at 25° C., and the remaining acidic solution was added dropwise over an hour. In the middle of the precipitation by acid, the whole mixture became pasty, and even when the stirring was stopped to leave the mixture to stand after completion of the precipitation by acid, no sedimentation or separation of crystals occurred. Filtration was possible, but filterability was very bad, taking 6 hours. The filtered crystals were washed twice with 1000 g of water, but poor in washing efficiency, and removal of neutralized salts was not enough (2.7 g of neutralized salts remained as a result of analysis). After pressing the crystal slurry, it was further washed twice with 1000 g of water followed by draining, and then was vacuum-dried at 80° C. for 24 hours, but it took a long time for drying. Meanwhile, the crystal slurry which was vacuum-dried after filtration had a liquid content of 75 wt %, and provided crystals in the form of fine powder that was difficult to dry, easy to scatter and bad in handleability (refers to FIG. 2). Finally, 365 g (1.46 mol, yield: 92.3 mol %, chemical purity 98.5%, optical purity 99% ee) of fine powdery crystals of S-CCA were obtained.

Comparative Example 2

In a 3 L glass vessel equipped with a condenser, 418 g (1.58 mol) of S-CCM obtained as in Example 1, 417.5 g of methanol, 82.0 g (2.05 mol) of NaOH and 1250 g of water were placed, and the mixture was allowed to react under nitrogen atmosphere at 80° C. for an hour under stirring. Next, under a temperature condition of 80° C., an acidic solution of 292.5 g (2.15 mol) of potassium hydrogen sulfate in 1250 g of water was added thereto until the pH reached 5. After insoluble matters were removed by filtration, the filtrate was kept at 35° C., and the remaining acidic solution was added dropwise over an hour. In the middle of the precipitation by acid, the whole mixture became pasty, and even when the stirring was stopped to leave the mixture to stand after completion of the precipitation by acid, no sedimentation or separation of crystals occurred. Filtration was possible, but filterability was very bad, taking 6 hours. The filtered crystals were washed twice with 1000 g of water, but poor in washing efficiency, and removal of neutralized salts was not enough (2.6 g of neutralized salts remained as a result of analysis). After pressing the crystal slurry, it was further washed twice with 1000 g of water followed by draining, and then was vacuum-dried at 80° C. for 24 hours, but it took along time for drying. Meanwhile, the crystal slurry which was vacuum-dried after filtration had a liquid content of 72 wt %, and provided crystals in the form of fine powder that was difficult to dry, easy to scatter and bad in handleability. Finally, 368 g (1.47 mol, yield: 93.1 mol %, chemical purity 98.6%, optical purity 99% ee) of fine powdery crystals of S-CCA were obtained.

Comparative Example 3

In a 3 L glass vessel equipped with a condenser, 418 g (1.58 mol) of S-CCM obtained as in Example 1, 417.5 g of methanol, 82.0 g (2.05 mol) of NaOH and 1250 g of water were placed, and the mixture was allowed to react under nitrogen atmosphere at 80° C. for an hour under stirring. Next, under a temperature condition of 80° C., an acidic solution of 292.5 g (2.15 mol) of potassium hydrogen sulfate in 1250 g of water was added thereto until the pH reached 5. After insoluble matters were removed by filtration, the filtrate was kept at 45° C., and the remaining acidic solution was added dropwise over an hour. In the middle of the precipitation by acid, the whole mixture became pasty, and even when the stirring was stopped to leave the mixture to stand after completion of the precipitation by acid, no sedimentation or separation of crystals occurred. Filtration was possible, but filterability was very bad, taking 6 hours. The filtered crystals were washed twice with 1000 g of water, but poor in washing efficiency, and removal of neutralized salts was not enough (2.7 g of neutralized salts remained as a result of analysis). After pressing the crystal slurry, it was further washed twice with 1000 g of water followed by draining, and then was vacuum-dried at 80° C. for 24 hours, but it took a long time for drying. Meanwhile, the crystal slurry which was vacuum-dried after filtration had a liquid content of 60 wt %, and provided crystals in the form of fine powder that was difficult to dry, easy to scatter and bad in handleability. Finally, 362 g (1.45 mol, yield: 91.5 mol %, chemical purity 98.7%, optical purity 99% ee) of fine powdery crystals of S-CCA were obtained.

Comparative Example 4

In a 3 L glass vessel equipped with a condenser, 418 g (1.58 mol) of S-CCM obtained as in Example 1, 417.5 g of methanol, 82.0 g (2.05 mol) of NaOH and 1250 g of water were placed, and the mixture was allowed to react under nitrogen atmosphere at 80° C. for an hour under stirring. Next, an acidic solution of 292.5 g (2.15 mol) of potassium hydrogen sulfate in 1250 g of water was added dropwise over an hour to the reaction solution which was kept at 25° C. In the middle of the precipitation by acid, the whole mixture became pasty, and even when the stirring was stopped to leave the mixture to stand after completion of the precipitation by acid, no sedimentation or separation of crystals occurred. Filtration was possible, but filterability was very bad, taking 6 hours. The filtered crystals were washed twice with 1000 g of water, but poor in washing efficiency, and removal of neutralized salts was not enough (2.7 g of neutralized salts remained as a result of analysis). After pressing the crystal slurry, it was further washed twice with 1000 g of water followed by draining, and then was vacuum-dried at 80° C. for 24 hours, but it took a long time for drying. Meanwhile, the crystal slurry which was vacuum-dried after filtration had a liquid content of 74 wt %, and provided crystals in the form of fine powder that was difficult to dry, easy to scatter and bad in handleability. Finally, 360 g (1.44 mol, yield: 91.1 mol %, chemical purity 98.2%, optical purity 99% ee) of fine powdery crystals of S-CCA were obtained.

Comparative Example 5

In a 3 L glass vessel equipped with a condenser, 418 g (1.58 mol) of S-CCM obtained as in Example 1, 417.5 g of methanol, 82.0 g (2.05 mol) of NaOH and 1250 g of water were placed, and the mixture was allowed to react under nitrogen atmosphere at 85° C. for an hour under stirring. Next, an acidic solution of 292.5 g (2.15 mol) of potassium hydrogen sulfate in 1250 g of water was added dropwise over an hour to the reaction solution which was kept at 85° C. When the stirring was stopped to leave the mixture to stand after completion of the precipitation by acid, it separated into an oil layer and an aqueous layer. When the temperature thereof was cooled to room temperature under stirring, the oil layer was crystallized at once and became a massive crystal. This was taken out and subjected to filtration to give crystals which were not uniform even in appearance. The filtered crystals were washed twice with 1000 g of water, and then vacuum-dried at 80° C. for 24 hours. Meanwhile, the crystal slurry which was vacuum-dried after filtration had a liquid content of 50 wt %, and provided crystals which were difficult to dry. Finally, 349 g (1.39 mol, yield: 88.3 mol %, chemical purity 98.0%, optical purity 99% ee) of crystals of S-CCA were obtained.

Comparative Example 6

In a 3 L glass vessel equipped with a condenser, 418 g (1.58 mol) of S-CCM obtained as in Example 1, 417.5 g of methanol, 126.4 g (3.16 mol) of NaOH and 1250 g of water were placed, and the mixture was allowed to react under nitrogen atmosphere at 40° C. for four hours under stirring. Next, an acidic solution of 451.7 g (3.32 mol) of potassium hydrogen sulfate in 1250 g of water was added thereto until the pH reached 5. After insoluble matters were removed by filtration, the filtrate was kept at 40° C., and the remaining acidic solution was added dropwise over an hour. In the middle of the precipitation by acid, the whole mixture became pasty, and even when the stirring was stopped to leave the mixture to stand after completion of the precipitation by acid, no sedimentation or separation of crystals occurred. Filtration was possible, but filterability was very bad, taking 6 hours. The filtered crystals were washed twice with 1000 g of water, but poor in washing efficiency, and removal of neutralized salts was not enough (2.6 g of neutralized salts remained as a result of analysis). After pressing the crystal slurry, it was further washed twice with 1000 g of water followed by draining, and then was vacuum-dried at 80° C. for 24 hours, but it took a long time for drying. Meanwhile, the crystal slurry which was vacuum-dried after filtration had a liquid content of 65 wt %, and provided crystals in the form of fine powder that was difficult to dry, easy to scatter and bad in handleability. Finally, 352 g (1.41 mol, yield: 89.0 mol %, chemical purity 96.9%, optical purity 99% ee) of crystals of S-CCA were obtained.

Comparative Example 7

In a 3 L glass vessel equipped with a condenser, 418 g (1.58 mol) of S-CCM obtained as in Example 1, 417.5 g of methanol, 126.4 g (3.16 mol) of NaOH and 1250 g of water were placed, and the mixture was allowed to react under nitrogen atmosphere at 40° C. for 4 hours under stirring. Next, under a temperature condition of 60° C., an acidic solution of 451.7 g (3.32 mol) of potassium hydrogen sulfate in 1250 g of water was added thereto until the pH reached 5, and then insoluble matters were removed by filtration. 1 g of seed crystals were added to the filtrate, and then the remaining acidic solution was added dropwise over an hour to cause precipitation by acid while keeping the filtrate at 60° C. After completion of the dropping, the stirring was stopped to precipitate crystals excellent in sedimentation separability. The crystals were filtered, and washed twice with 1250 mL of water. The resulting crystal slurry had a liquid content of 33 wt %, and after drying, yielded 359 g (1.43 mol, yield: 90.8 mol %, chemical purity 97.9%, optical purity 99% ee) of crystals of S-CCA.

TABLE 1

A table summarizing reaction conditions, and yield and purity of S-CCA in Examples and Comparative Examples.

| | Reaction Conditions | | | | | | S-CCA | | |
|---|---|---|---|---|---|---|---|---|---|
| | Ester hydrolysis | | Filtration of insoluble matters | | Precipitation by acid | | | | |
| | Reaction Temperature (° C.) | Reaction Time (hr) | Solution pH | Filtration Temperature (° C.) | Addition of seed crystals | Temperature of precipitation by acid (° C.) | Yield (%) | Chemical purity (%) | Optical purity (% ee) |
| Example 1 | 80 | 1 | 5 | 80 | None | 60 | 92.4 | 99.7 | 99 |
| Example 2 | 80 | 1 | 5 | 80 | None | 50 | 93.0 | 99.5 | 99 |
| Example 3 | 80 | 1 | 5 | 80 | None | 70 | 91.8 | 99.6 | 99 |
| Example 4 | 80 | 1 | 5 | 80 | None | 80 | 92.6 | 99.2 | 99 |
| Example 5 | 80 | 1 | 5 | 80 | Added | 60 | 93.0 | 99.7 | 99 |
| Example 6 | 80 | 1 | 7 | 80 | None | 60 | 93.0 | 99.5 | 99 |
| Example 7 | 80 | 1 | 5 | 60 | None | 60 | 94.9 | 99.6 | 99 |
| Example 8 | 80 | 1 | 5 | 80 | Added | 80 | 93.3 | 99.2 | 99 |
| Example 9 | 60 | 2 | 5 | 60 | Added | 60 | 92.6 | 99.0 | 99 |
| Example 10 | 50 | 3 | 5 | 50 | Added | 50 | 92.1 | 98.9 | 99 |
| Comparative Example 1 | 80 | 1 | 5 | 80 | None | 25 | 92.3 | 98.5 | 99 |
| Comparative Example 2 | 80 | 1 | 5 | 80 | None | 35 | 93.1 | 98.6 | 99 |
| Comparative Example 3 | 80 | 1 | 5 | 80 | None | 45 | 91.5 | 98.7 | 99 |
| Comparative Example 4 | 80 | 1 | | None | None | 25 | 91.1 | 98.2 | 99 |
| Comparative Example 5 | 85 | 1 | | None | None | 85 | 88.3 | 98.0 | 99 |
| Comparative Example 6 | 40 | 4 | 5 | 40 | None | 40 | 87.3 | 96.9 | 99 |
| Comparative Example 7 | 40 | 4 | 5 | 60 | Added | 60 | 90.8 | 97.9 | 99 |

INDUSTRIAL APPLICABILITY

According to the present invention, S-(−)-6-hydroxy-2,5,7,8-tetramethylchromane-2-carboxylic acid excellent in crystal properties, chemical purity and optical purity can be produced efficiently in high yield. The S-(−)-6-hydroxy-2,5,7,8-tetramethylchromane-2-carboxylic acid, especially, high-purity one is extremely important as raw materials for vitamins, or drugs such as anti-inflammatory agents and anti-allergy agents.

The invention claimed is:

1. A method for producing S-(-)-6-hydroxy-2,5,7,8-tetramethylchromane-2-carboxylic acid in an aqueous solvent by hydrolysis of an S-(-)-6-hydroxy-2,5,7,8-tetramethylchromane-2-carboxylic acid ester represented by general formula (1), which comprises (A) hydrolyzing an S-(-)-6-hydroxy-2,5,7,8-tetramethylchromane-2-carboxylic acid ester represented by general formula (1) under a basic condition for 1-3 hours, then (B) removing insoluble matters contained in the reaction solution resulting from the hydrolysis, and (C) adding an acid to the resulting solution under a temperature condition of 50-80° C. to effect crystallization

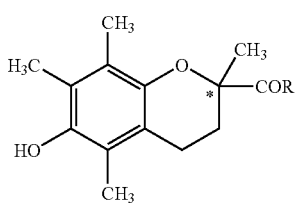

(1)

wherein R in general formula (1) represents an alkyl group or aryl group.

2. A method for producing S-(-)-6-hydroxy-2,5,7,8-tetramethylchromane-2-carboxylic acid, according to claim 1, in which the aqueous solvent comprises an alcohol.

3. A method for producing S-(-)-6-hydroxy-2,5,7,8-tetramethylchromane-2-carboxylic acid, according to claim 2, in which the alcohol is methanol.

4. A method for producing S-(-)-6-hydroxy-2,5,7,8-tetramethylchromane-2-carboxylic acid, according to claim 1, in which the removal of insoluble matters contained in the reaction solution resulting from the hydrolysis in (B) is conducted after adjusting a pH of the reaction solution to 5-7.

5. A method for producing S-(-)-6-hydroxy-2,5,7,8-tetramethylchromane-2-carboxylic acid, according to claim 1, in which crystals of S-(-)-6-hydroxy-2,5,7,8-tetramethylchromane-2-carboxylic acid are added as seed crystals when an acid is added to the resulting solution to effect crystallization in (C).

6. A method for producing S-(-)-6-hydroxy-2,5,7,8-tetramethylchromane-2-carboxylic acid, according to claim 2, in which said alcohol is methanol in an amount of 0.1 to 1-fold amount by weight relative to water.

7. A method for producing S-(-)-6-hydroxy-2,5,7,8-tetramethylchromane-2-carboxylic acid, according to claim 1, in which said hydrolyzing an S-(-)-6-hydroxy-2,5,7,8-tetramethylchromane-2-carboxylic acid ester is conducted under a temperature condition of 50-80° C.

8. A method for producing S-(-)-6-hydroxy-2,5,7,8-tetramethylchromane-2-carboxylic acid, according to claim 1, in which said removing insoluble matters is conducted under a temperature condition of 50-80° C.

9. A method for producing S-(-)-6-hydroxy-2,5,7,8-tetramethylchromane-2-carboxylic acid in an aqueous solvent by hydrolysis of an S-(-)-6-hydroxy-2,5,7,8-tetramethylchromane-2-carboxylic acid ester represented by general formula (1), which comprises (A) hydrolyzing an S-(-)-6-hydroxy-2,5,7,8-tetramethylchromane-2-carboxylic acid ester represented by general formula (1) under a basic condition for 1-3 hours under a temperature condition of 50-80° C., then (B) removing insoluble matters contained in the reaction solution resulting from the hydrolysis under a temperature condition of 50-80° C., and (C) adding an acid to the resulting solution under a temperature condition of 50-80° C. to effect crystallization

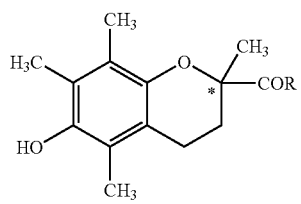

(1)

wherein R in general formula (1) represents an alkyl group or aryl group.

* * * * *